United States Patent
Alon

(10) Patent No.: US 12,023,247 B2
(45) Date of Patent: Jul. 2, 2024

(54) REDUCING THE DIAMETER OF A CARDIAC VALVE ANNULUS WITH INDEPENDENT CONTROL OVER EACH OF THE ANCHORS THAT ARE LAUNCHED INTO THE ANNULUS

(71) Applicant: Edwards Lifesciences Corporation, Irvine, CA (US)

(72) Inventor: David Alon, Zichron Yaacov (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 239 days.

(21) Appl. No.: 17/323,644

(22) Filed: May 18, 2021

(65) Prior Publication Data

US 2021/0361431 A1 Nov. 25, 2021

Related U.S. Application Data

(60) Provisional application No. 63/027,640, filed on May 20, 2020.

(51) Int. Cl.
*A61F 2/24* (2006.01)
*A61M 25/01* (2006.01)

(52) U.S. Cl.
CPC ....... *A61F 2/2466* (2013.01); *A61M 25/0105* (2013.01); *A61F 2220/0016* (2013.01); *A61M 2025/0166* (2013.01)

(58) Field of Classification Search
CPC .............. A61M 25/0105; A61F 2250/0007
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |
| 3,840,018 A | 10/1974 | Heifetz |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Melanie R Tyson
*Assistant Examiner* — Cassidy N Stuhlsatz
(74) *Attorney, Agent, or Firm* — Thomas C. Richardson

(57) ABSTRACT

A device (e.g., an annulus-constricting device) with N anchors may be affixed to a cardiac valve annulus as follows. First, the device is delivered to the vicinity of the annulus via a catheter. Next, the position and layout of the device is adjusted via the catheter. Next, only those anchors which are properly positioned are driven into the annulus or tissue adjacent to the annulus. The remaining anchors remain unlaunched at this point. The unlaunched anchors are subsequently moved into a good position using either a manipulating tool or catheter-steering techniques, after which they are driven into the annulus or tissue adjacent to the annulus.

20 Claims, 14 Drawing Sheets

(56) References Cited

U.S. PATENT DOCUMENTS

| | | |
|---|---|---|
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |

(56) References Cited

U.S. PATENT DOCUMENTS

| | | |
|---|---|---|
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |

(56) References Cited

U.S. PATENT DOCUMENTS

| | | |
|---|---|---|
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,517,130 B1 | 12/2016 | Alon et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,143,553 B2 | 12/2018 | Alon et al. |
| 10,206,776 B2 | 2/2019 | Alon |
| 10,368,852 B2 | 8/2019 | Gerhardt et al. |
| 10,575,952 B2 | 3/2020 | Alon |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |

(56) References Cited

U.S. PATENT DOCUMENTS

| | | |
|---|---|---|
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |

(56) References Cited

U.S. PATENT DOCUMENTS

| | | |
|---|---|---|
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |

(56) References Cited

U.S. PATENT DOCUMENTS

| | | |
|---|---|---|
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1* | 5/2016 | Alon ............... A61F 2/2466 623/2.4 |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012176195 A3 | 3/2013 |
| WO | 2014064964 A3 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

(56) References Cited

OTHER PUBLICATIONS

Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results 04yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2): 100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. Vol 53:271-303, 1978.

* cited by examiner

REDUCING THE DIAMETER OF A CARDIAC VALVE ANNULUS WITH INDEPENDENT CONTROL OVER EACH OF THE ANCHORS THAT ARE LAUNCHED INTO THE ANNULUS

CROSS REFERENCE TO RELATED APPLICATIONS

This application claims the benefit of U.S. Provisional Application 63/027,640, filed May 20, 2020, which is incorporated herein by reference in its entirety.

BACKGROUND

U.S. Pat. Nos. 9,517,130, 10,143,553, 10,206,776, and 10,575,952, each of which is incorporated by reference, describes a variety of approaches for (a) affixing a cord to a cardiac valve annulus or to adjacent tissue (e.g., leaflets of the valve) using a plurality of anchors and (b) getting the cord in position before the anchors are driven into the tissue. After the cord has been affixed, tissue healing strengthens the bond between the annulus and the anchors over time (e.g., 4-8 weeks). In some cases, tissue healing also strengthens a bond between the annulus and a sleeve that promotes tissue ingrowth that surrounds the cord. After the bond has been strengthened, the cord can be used to reduce the size of the annulus.

As best described in U.S. Pat. No. 10,206,776, each of the anchors that is driven into the tissue has a corresponding anchor launcher, and each of the anchor launchers has its own individual actuator (e.g., a pull wire). The '776 patent also describes a mechanism for triggering all of the anchor launchers by pulling on a set of pull wires that serve as the actuators for the anchor launchers. This can be done either sequentially (i.e., by triggering one anchor launcher at a time in rapid succession) or simultaneously (i.e., by triggering all of the anchor launchers simultaneously). But in either situation, the mechanism for triggering the anchor launchers always triggered each and every one of the anchor launchers.

In view of this arrangement, the cord, the anchors, and the anchor launchers in the '776 patent had to be positioned very precisely before the anchors were launched. For if one or more anchors was not positioned close enough to the target tissue at the moment those anchors were launched out of the respective anchor launchers, those anchors would not become properly embedded in the annulus or the adjacent tissue.

SUMMARY OF THE INVENTION

One aspect of the invention is directed to a first method of affixing a device to a cardiac valve annulus. The first method comprises delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus. Subsequent to the delivering, a position and layout of the flexible cord is adjusted via the catheter until the position and layout of the flexible cord corresponds the annulus. Subsequent to the adjusting, a first subset of the N anchors which are positioned such that the respective anchor launcher can successfully drive the respective anchor into the annulus or tissue adjacent to the annulus are identified, wherein the first subset includes fewer than N anchors. Subsequent to the identifying, a first subset of the N anchor launchers that corresponds to the first subset of the N anchors is actuated, so that the first subset of the N anchor launchers drive the first subset of the N anchors into the annulus or tissue adjacent to the annulus. The first method also comprises introducing a manipulating tool via the catheter to the vicinity of the annulus. Subsequent to the actuating of the first subset of the N anchor launchers, for each of the N anchors that have not yet been driven into the annulus or tissue adjacent to the annulus, (a) the manipulating tool is used to move the anchor to a position where the respective anchor launcher can successfully drive the anchor into the annulus or tissue adjacent to the annulus, and (b) the respective anchor launcher is actuated so that the respective anchor launcher drives the anchor into the annulus or tissue adjacent to the annulus.

In some instances of the first method, each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

In some instances of the first method, the identifying step comprises at least one of echo imaging and fluoro imaging. In some instances of the first method, the identifying step comprises determining whether a contact probe that is affixed to each of the anchor launchers is making contact with tissue. In some instances of the first method, the actuating of the first subset of the N anchor launchers comprises actuating the entire first subset of the N anchor launchers substantially simultaneously. In some instances of the first method, the step of adjusting a position and layout of the flexible cord comprises inflating a balloon. In some instances of the first method, the first subset includes at least two anchors.

Another aspect of the invention is directed to a second method of affixing a device to a cardiac valve annulus. The second method comprises delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus. Subsequent to the delivering, a position and layout of the flexible cord is adjusted via the catheter until the position and layout of the flexible cord corresponds the annulus. Subsequent to the adjusting, a first subset of the N anchors which are positioned such that the respective anchor launcher can successfully drive the respective anchor into the annulus or tissue adjacent to the annulus is identified, wherein the first subset includes fewer than N anchors. Subsequent to the identifying, a first subset of the N anchor launchers that corresponds to the first subset of the N anchors is actuated, so that the first subset of the N anchor launchers drive the first subset of the N anchors into the annulus or tissue adjacent to the annulus. Subsequent to the actuating of the first subset of the N anchor launchers, for each of the N anchors that have not yet been driven into the annulus or tissue adjacent to the annulus, (a) catheter steering techniques are used to adjust a position of a respective corresponding anchor launcher to a position where the respective corresponding anchor launcher can successfully drive the anchor into the annulus or tissue adjacent to the annulus, and (b) the respective corresponding anchor launcher is actuated so that the respective corresponding anchor launcher drives the anchor into the annulus or tissue adjacent to the annulus.

In some instances of the second method, steps (a) and (b) are performed at least twice, and steps (a) and (b) are repeated until all of the anchors have been driven into the annulus or tissue adjacent to the annulus.

In some instances of the second method, each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

In some instances of the second method, the identifying step comprises at least one of echo imaging and fluoro imaging. In some instances of the second method, the identifying step comprises determining whether a contact probe that is affixed to each of the anchor launchers is making contact with tissue. In some instances of the second method, the actuating of the first subset of the N anchor launchers comprises actuating the entire first subset of the N anchor launchers substantially simultaneously. In some instances of the second method, the first subset includes at least two anchors.

Another aspect of the invention is directed to a third method of affixing a device to a cardiac valve annulus. The third method comprises delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus. The third method also comprises introducing a manipulating tool via the catheter to the vicinity of the annulus. For each of the N anchors in turn, (a) the manipulating tool is used to move the anchor to a position where the respective anchor launcher can successfully drive the anchor into the annulus or tissue adjacent to the annulus, and (b) the respective anchor launcher is actuated so that the respective anchor launcher drives the anchor into the annulus or tissue adjacent to the annulus.

In some instances of the third method, each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

Some instances of the third method further comprise using at least one of echo imaging and fluoro imaging to determine the position of the anchors while the manipulating tool is being used to move the anchors. Some instances of the third method further comprise determining whether a contact probe that is affixed to each of the anchor launchers is making contact with tissue. Some instances of the third method further comprise, subsequent to the delivering, adjusting a position and layout of the flexible cord via the catheter until the position and layout of the flexible cord corresponds the annulus.

In some instances of the third method, the step of adjusting a position and layout of the flexible cord comprises inflating a balloon.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

The embodiments described herein significantly relax the requirements to position the cord, the anchors and the anchor launchers precisely before the anchors are launched. This is accomplished by positioning the cord up against the annulus when the anchors are ready to launch, then identifying which anchors are properly positioned so that they can be successfully driven into the annulus or adjacent tissue. This identification may be implemented, for example, using echo imaging, fluoro imaging, or contact probes that are affixed to each of the anchor launchers.

Next, only those anchor launchers that are in a position where the corresponding anchors can be successfully driven into the annulus or adjacent tissue are actuated. This will drive the majority of the anchors into the annulus or adjacent tissue. But a small number of anchors will not be launched, and will remain in their respective anchor launchers. In some embodiments, a manipulator tool is then introduced, and is used to move each of the unlaunched anchors to a position where it can be successfully driven into the annulus. In other embodiments, each of the unlaunched anchors is moved to a position where it can be successfully driven into the annulus using catheter-steering techniques.

Unlike the prior art approach described in U.S. Pat. No. 10,206,776, in which a single user-operated control triggers all of the actuators, the actuators in the embodiments described herein can be controlled individually. Assume, for example, that the anchor launchers described in connection with FIG. 54A and 54B of U.S. Pat. No. 10,206,776, which is incorporated herein by reference, are being used. Those anchor launchers are triggered by pulling on an actuation wire, and an individual actuation wire is provided for each anchor launcher.

Figure 1:
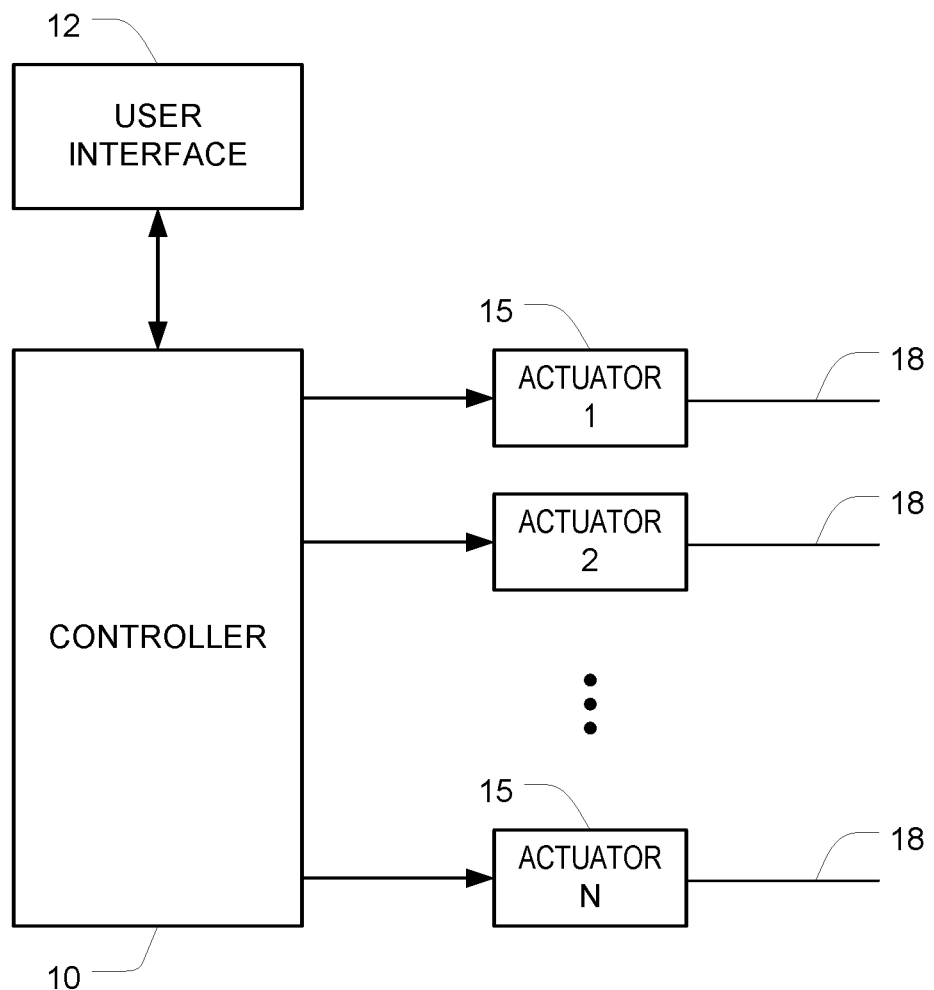
FIG. 1 depicts one example of an approach for implementing individually-controllable actuators.

FIG. 1 depicts one example of an approach for implementing individually-controllable actuators. In this approach, an individually controllable actuator 15 is provided for each anchor launcher, and each of those individually controllable actuators 15 pulls on a respective one of the actuation wires 18. The number of actuators 15 will correspond to the number of anchors that are used to affix the cord to the cardiac valve annulus or to adjacent tissue. For example, in those embodiments where N anchors are used to affix the cord (where N is an integer), there will be a corresponding number (N) of anchor launchers, and each of those N anchor launchers will have its own individual actuation wire 18.

Because the actuators 15 are individually controllable, it now becomes possible to actuate any desired subset of the N anchor launchers without actuating the rest of the anchor launchers. Assume, for example, that N=8 and the operator has decided to launch anchors #1, #2, #3, #5, #6, and #8, but not to launch anchors #4 and #7. This decision may be based, for example, on echo imaging, fluoro imaging, or another modality of imaging. The user informs the system which anchors should be launch via user interface 12, and the user interface 12 conveys the list of anchors to be launched to the controller 10. Alternatively, the decision of which launchers should be launched may be based on information received from a set of N contact sensors (not shown), each of which is configured to detect when the distal end of a respective anchor launcher is making contact with tissue. When contact sensors are provided, the contact sensors convey the list of anchors that should be launched to the controller 10.

The user interface 12 has a "launch" button (or other user control). When the user presses the "launch" button, the user interface 12 sends a signal to the controller 10, requesting launching of the previously identified subset of anchors (in the current example, this would be anchors #1, #2, #3, #5, #6, and #8). The controller 10 effectuates launching of the identified subset of anchors by sending an appropriate command to actuators (15) #1, #2, #3, #5, #6, and #8, but not sending that command to actuators (15) #4 and #7. Upon receiving the command, only actuators (15) #1, #2, #3, #5, #6, and #8 will pull their respective actuation wires 18. Those actuation wires 18 will actuate only anchor launchers #1, #2, #3, #5, #6, and #8, and those anchor launchers will launch their respective anchors into the cardiac valve annulus or adjacent tissue. Meanwhile, because anchor launchers #4 and #7 have not been actuated, anchors #4 and #7 will remain unlaunched (for the time being).

At a subsequent time, the unlaunched anchors can be driven into the cardiac valve annulus or adjacent tissue by actuating their respective anchor launchers individually. The controller 10 can accomplish this, for example, as follows: First, the controller 10 sends an appropriate command to actuator (15) #4 only. Upon receiving the command, only actuator #4 will pull its respective actuation wire 18. That actuation wire will actuate only anchor launcher #4, which will launch anchor #4 into the cardiac valve annulus or adjacent tissue. Subsequently, the controller 10 sends an appropriate command to actuator #7 only. Upon receiving the command, only actuator (15) #7 will pull its respective actuation wire 18. That actuation wire will actuate only anchor launcher #7, which will launch anchor #7 into the cardiac valve annulus or adjacent tissue.

Figure 2A:
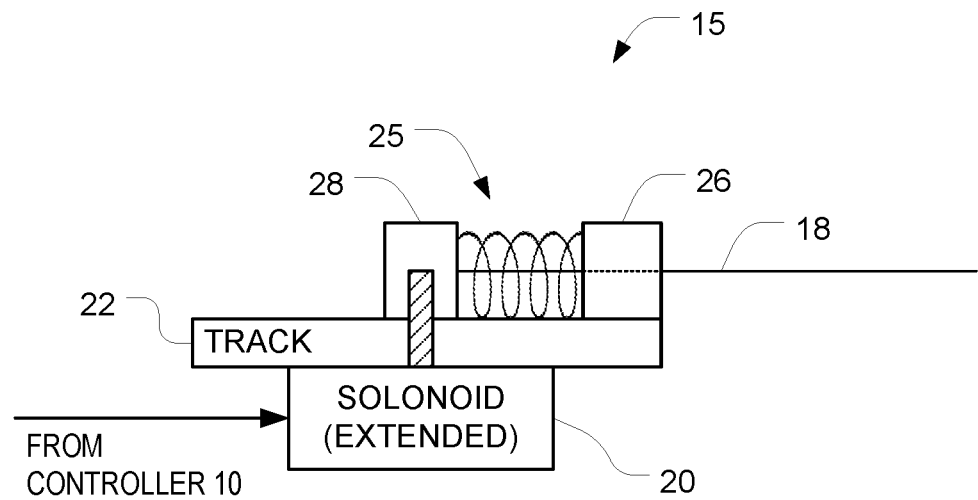
FIGS. 2A and 2B depict one example of a mechanism for implementing any given one of the actuators depicted in FIG. 1.
Figure 2B:
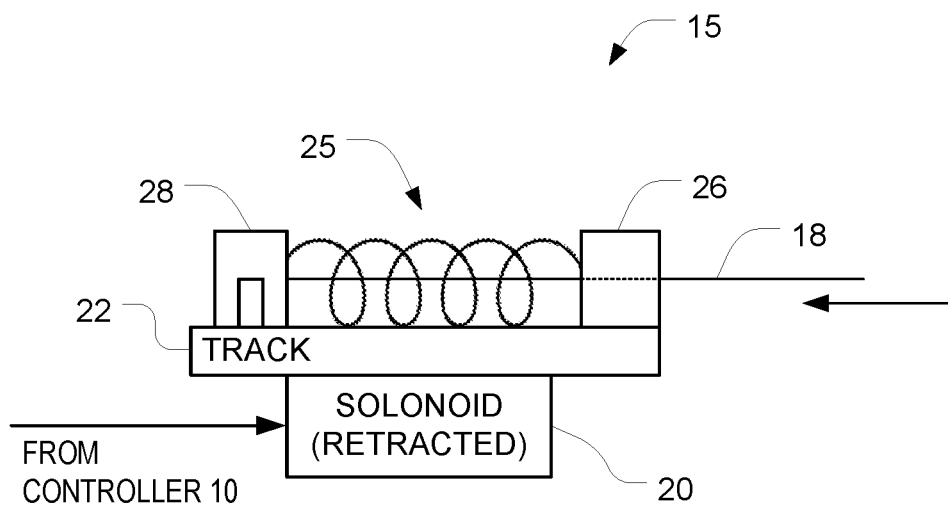

FIGS. 2A and 2B depict one example of a mechanism for implementing any given one of the actuators 15 depicted in FIG. 1. In this example, the actuator 15 relies on a spring 25 to pull the actuation wire 18. Initially, as seen in FIG. 2A, the spring 25 is held in a compressed state between base 26 and cap 28. The base 26 is permanently affixed to a track 22, and the cap 28 is slidably connected to the track 22. Solenoid 20 has a plunger that, in its extended state, prevents the cap 28 from moving. The actuation wire 18 is affixed to the cap 28 so that movement of the cap 28 to the left will pull the actuation wire 18 to the left. As long as the cap 28 remains in the position depicted in FIG. 2A, the actuation wire 18 will not be pulled; the anchor launchers will not be actuated; and the anchors will remain in position within their respective anchor launchers.

Turning now to FIG. 2B, when the controller 10 (depicted in FIG. 1) sends an appropriate signal to the solenoid 20, the plunger of the solenoid retracts. Once the plunger retracts, nothing remains to prevent the cap 28 from moving with respect to the track 22, and the spring 25 is now free to expand to its relaxed state. The spring 25 pushes the cap 28 to the left; and because the actuation wire 18 is connected to the cap 28, the cap 28 will pull the actuation wire 18 to the left. This will actuate the corresponding anchor launcher so that it ejects the corresponding anchor and drives it into the tissue.

Of course, the solenoid-based embodiment depicted in FIGS. 2A and 2B is only one example of a suitable mechanism for implementing the actuators 15 depicted in FIG. 1; and a wide variety of alternative approaches for individually actuating each of the anchor launchers 40 will be apparent to persons skilled in the relevant art.

FIGS. 3-9 depict an example of affixing an annulus-constricting device to a cardiac valve annulus. In this example, N=10, so there are 10 anchors 50 distributed about the flexible cord 30, and each of those 10 anchors 50 is slidably affixed with respect to the flexible cord 30. In the embodiment depicted in FIGS. 3-9, an optional sleeve 35 made from a material that accepts tissue ingrowth surrounds the flexible cord 30.

Examples of how to construct the anchors 50 and how to slidably affix the anchors 50 to the flexible cord 30 can be found, for example, in U.S. Pat. Nos. 9,517,130 and 10,206,776, each of which is incorporated herein by reference in its entirety. The slidable affixation of the anchors to the cord may be direct (e.g., when the cord is threaded directly through a slot in each of the anchors) or indirect (e.g., when the cord is threaded through an eyelet, and a slot in each of the anchors slides with respect to the eyelet). There are also 10 anchor launchers 40, and each of those 10 anchor launchers 40 is configured to, upon actuation, drive a respective one of the 10 anchors 50 into the annulus or tissue adjacent to the annulus. Examples of suitable anchor launchers 40 can be found, for example, in U.S. Pat. No. 10,206, 776.

Figure 3:
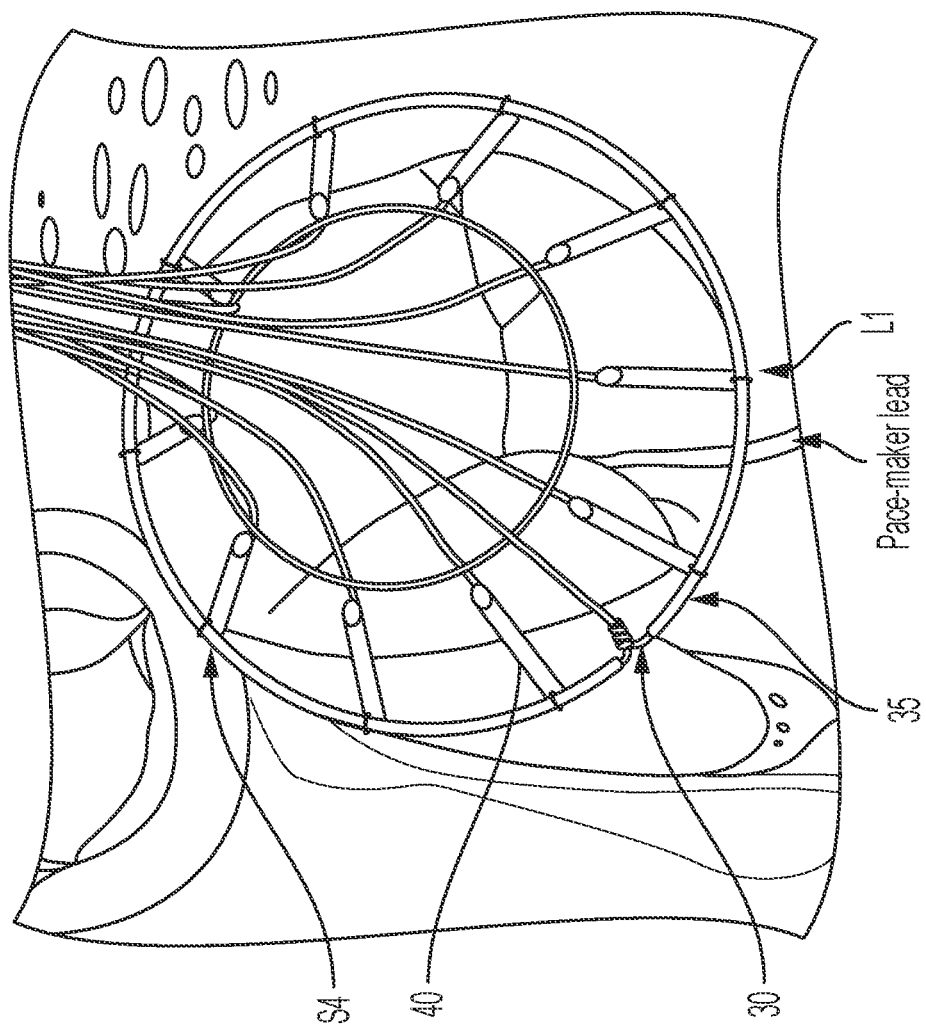
FIG. 3 depicts an example of an annulus-constricting device positioned next to a cardiac valve annulus prior to launching of the anchors, where only 8 of the 10 anchor launchers are positioned for launching their respective anchors.

The flexible cord 30, the anchors 50, and the anchor launchers 40 are delivered to the vicinity of the annulus via a catheter (e.g., as described in U.S. Pat. No. 10,575,952, which is incorporated herein by reference in its entirety). Subsequent to the delivering, the position and layout of the flexible cord 30 is adjusted via the catheter until the position and layout of the flexible cord 30 corresponds the annulus, as depicted in FIG. 3. Optionally, an inflatable balloon (not shown) positioned between the arms that support the anchor launchers 40 may be used to help put the flexible cord 30 into a shape that approximates the shape of the annulus. The adjusting of the position of the flexible cord 30 may be implemented by an operator (e.g., using conventional catheter steering techniques) based on visual feedback obtained, for example, using echo imaging or fluoro imaging. Alternatively or additionally, the adjusting of the position of the flexible cord 30 may be implemented by an operator based on signals received from a set of contact probes (not shown) which are positioned on each anchor launcher 40 and provide a real time indication of contact with the tissue (e.g., by sending an electrical signal to the controller 10 shown in FIG. 1).

In the example depicted in FIG. 3, only two anchor launchers 40 are NOT positioned such that the respective anchor launcher can successfully drive the respective anchor into the annulus or tissue adjacent to the annulus, because those two anchor launchers 40 are out of contact with corresponding tissue. This may occur, for example, due to surface variations like a small landing zone in the septal region (for the anchor launcher 40 labeled S4) or due to a pacemaker lead in a posterior region (for the anchor launcher 40 labeled L1). The remaining eight anchor launchers 40 ARE positioned such that the respective anchor launcher can successfully drive the respective anchor into the annulus or tissue adjacent to the annulus, because those eight anchor launchers 40 are in contact (or at least close enough) with corresponding tissue.

Subsequent to the position adjusting, a first subset of the 10 anchors 50 (i.e., those anchors which ARE positioned such that the respective anchor launcher can successfully drive the respective anchor into the annulus or tissue adjacent to the annulus) is identified. The first subset includes fewer than 10 anchors 50 (i.e., 8 anchors 50 in the illustrated embodiment). The identification may be accomplished, for example, using echo imaging, fluoro imaging, or based on signals received from the contact probes (not shown). In some preferred embodiments (including this example in which the first subset includes 8 anchors), the first subset includes at least two anchors. But in other embodiments, the first subset could include only a single anchor.

Subsequent to the identifying, a first subset of the anchor launchers (i.e., 8 anchor launchers 40 in the illustrated embodiment) that corresponds to the first subset of the anchors 50 is actuated. This causes the first subset of the anchor launchers 40 to drive the first subset of the anchors 50 into the annulus or tissue adjacent to the annulus. In the illustrated embodiment, the total number of anchor launchers 40 is 10, and the first subset includes 8 anchors 50. This means that only 2 anchors 50 have not been launched at this point in the procedure.

Figure 4A:
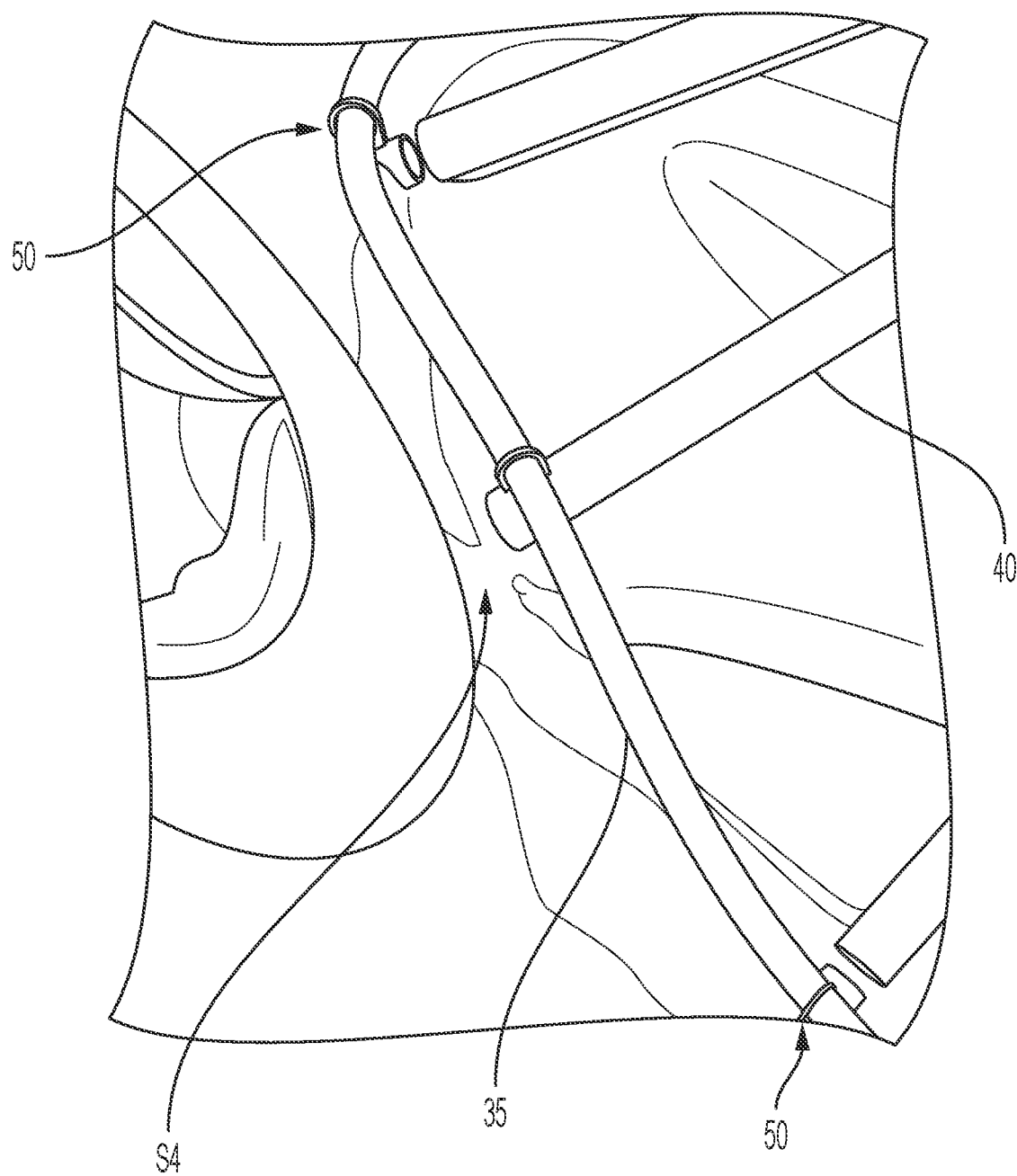
FIGS. 4A, 4B depict two detail views of the FIG. 3 embodiment after eight anchors have been launched and two anchors have not been launched.
Figure 4B:
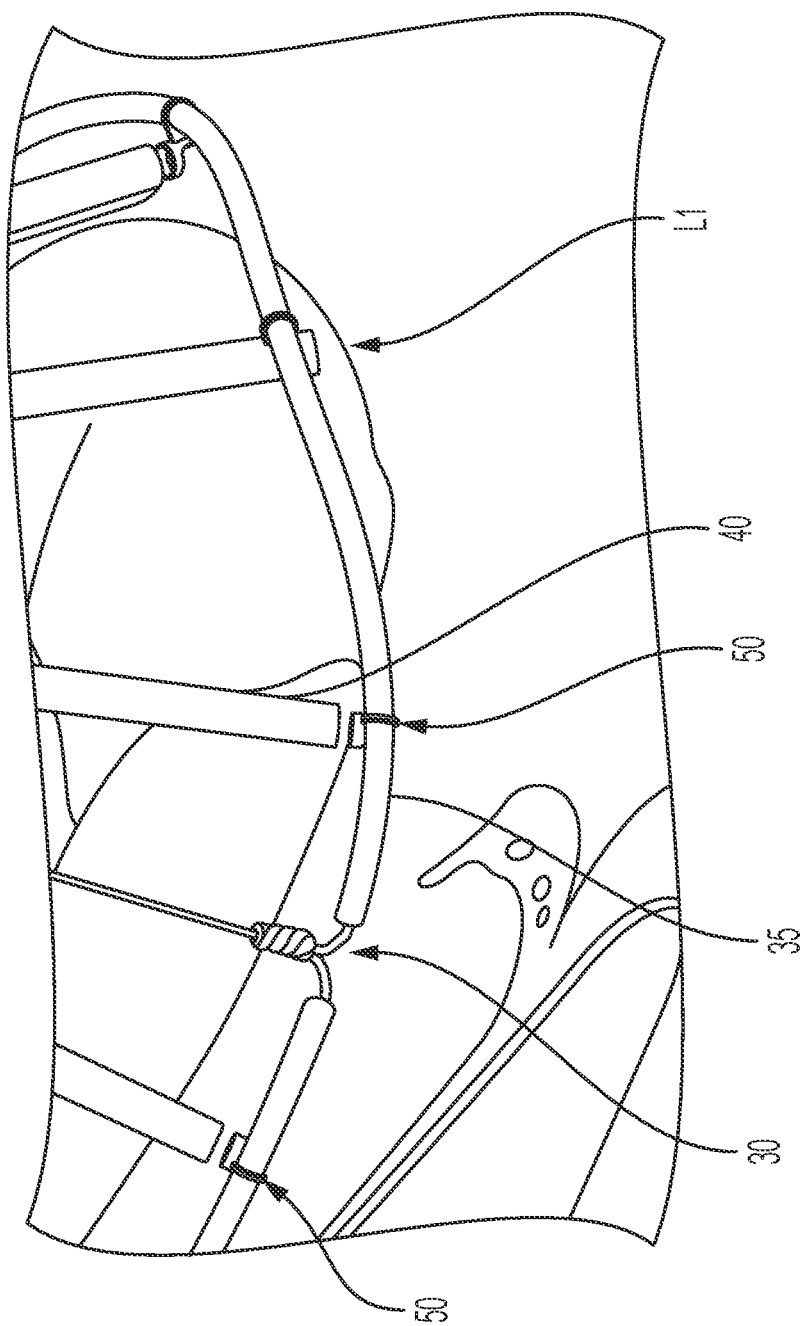
Figure 5:
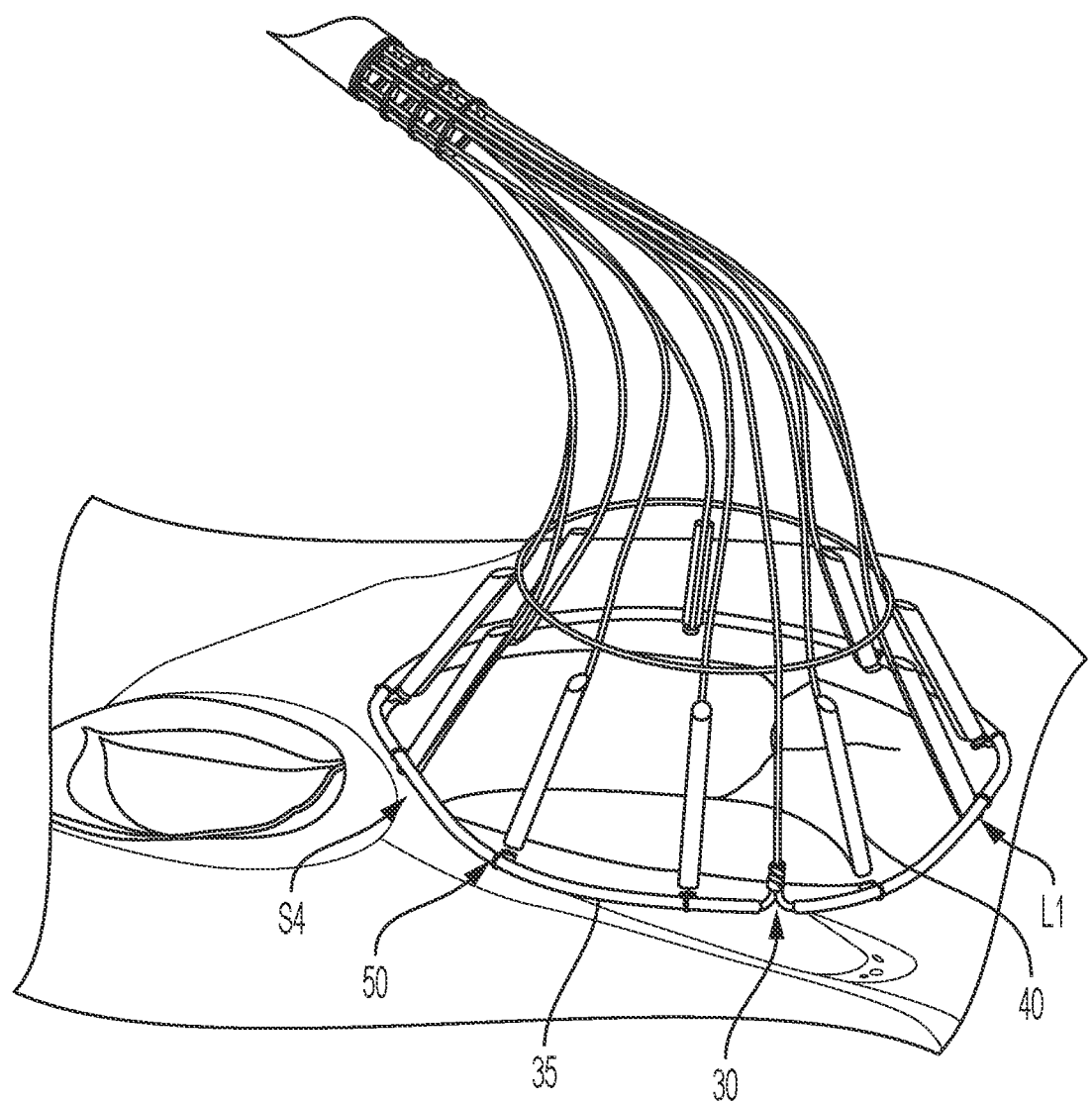
FIG. 5 depicts an overall view of the FIG. 3 embodiment after eight anchors have been launched and two anchors have not been launched.

Turning now to FIGS. 4A, 4B, and 5 in the illustrated embodiment, the two unlaunched anchors 50 at this point in the procedure correspond to the anchor launchers 40 labeled L1 and S4. The remaining eight anchors 50 have been driven into the annulus or adjacent tissue by the corresponding anchor launchers 40. In those embodiments where a balloon (not shown) was used to help bring the flexible cord 30 into position, the balloon should be deflated and withdrawn at this point in the procedure.

At this point in the procedure, the scaffold of arms that support the anchor launchers may collapse (fully or partially) because most of the anchors 50 that are attached to the flexible cord 30 are no longer held in place by their respective anchor launchers 40. Alternatively, in some embodiments, the scaffold of arms may be made from a soft metal that retains its shape after the balloon is removed and the majority of the anchors 50 have been launched.

Figure 6:
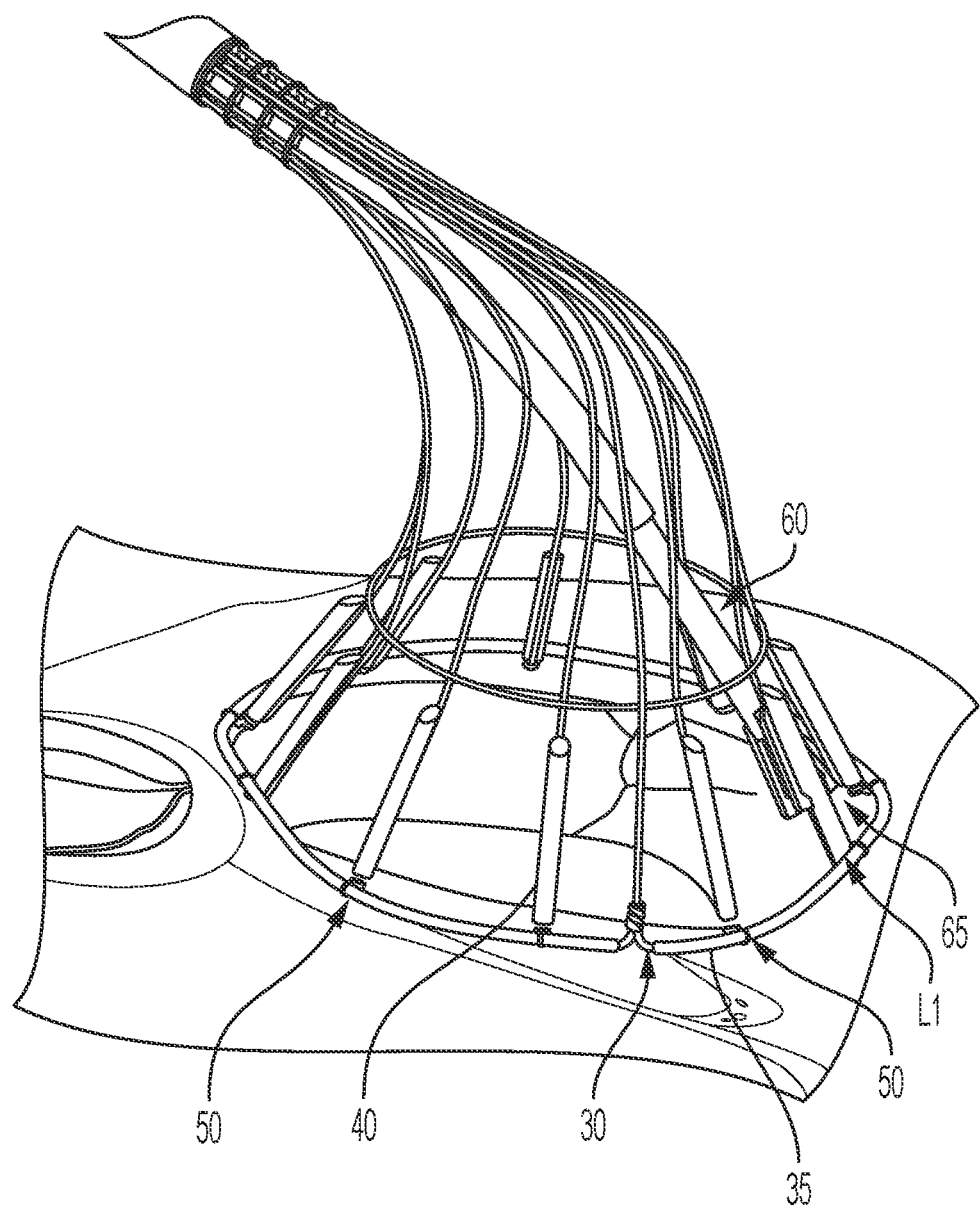
FIG. 6 depicts a manipulating tool that is being used to reposition the ninth anchor.

Next, as seen in FIG. 6, a manipulating tool 60 is introduced to the vicinity of the annulus via the catheter. The distal end of the manipulating tool 60 has a grabber 65 with jaws that can be opened and closed by the health practitioner. (As used herein, "distal" is further away from the practitioner who is operating the apparatus, and "proximal" is closer to the practitioner.) The grabber 65 is shaped and dimensioned to grab onto any of the anchor launchers 40 and subsequently manipulate the anchor launcher 40 to a desired position (i.e., to a position where the corresponding anchor 50 can be driven into the annulus or adjacent tissue). Manipulation of the position of the grabber 65 and the opening and closing of the jaws of the grabber 65 is controlled by the practitioner using a set of proximal controls (not shown).

Figure 7:
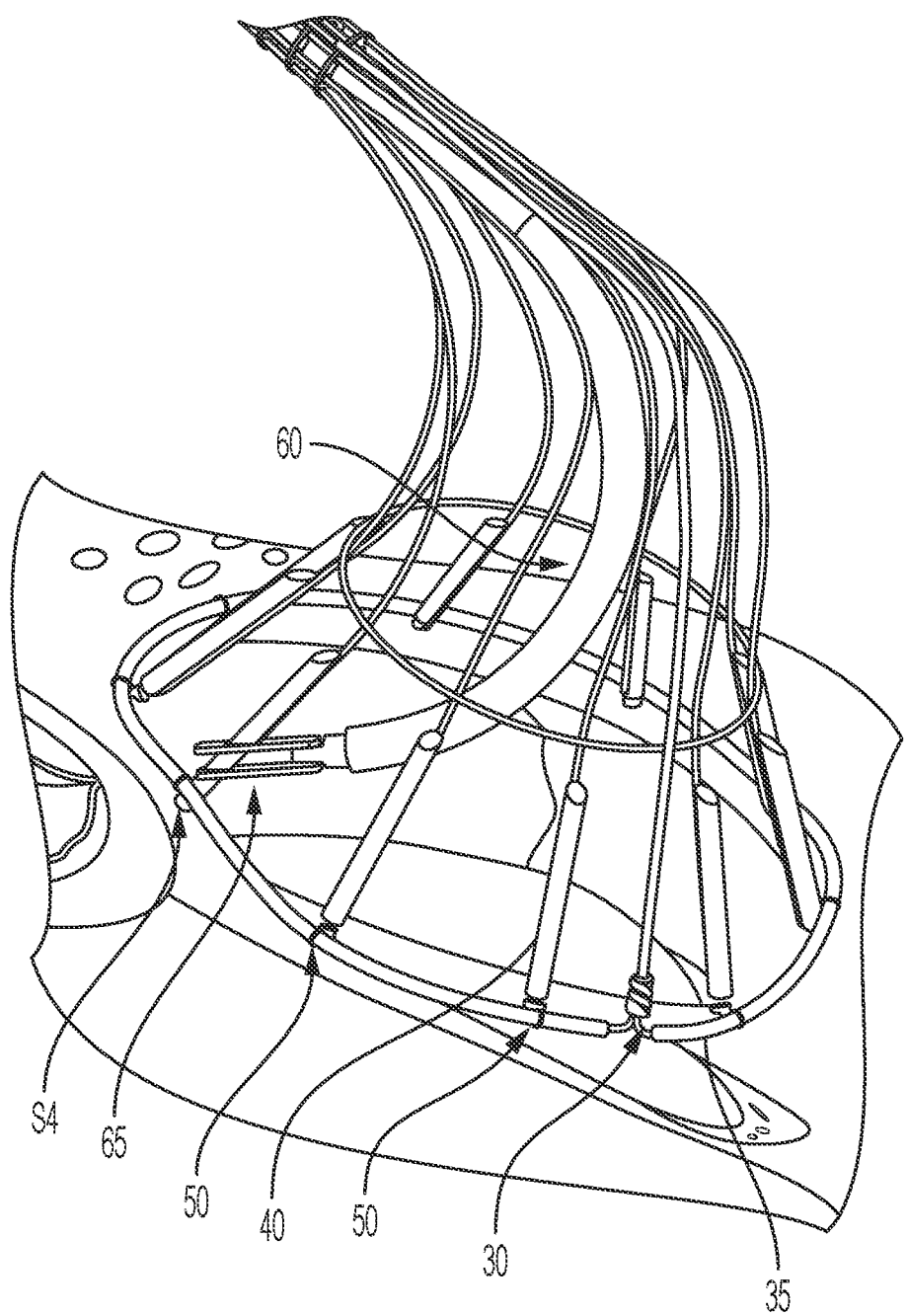
FIG. 7 depicts the manipulating tool that is being used to reposition the tenth anchor.

Subsequent to the actuating of the 8 anchor launchers 40 in the illustrated embodiment, for each of the 10 anchors 50 that have not yet been driven into the annulus or tissue adjacent to the annulus (i.e., for the 2 unlaunched anchors 50 in the illustrated embodiment), (a) the manipulating tool 60 is used to move the anchor to a position where the respective anchor launcher 40 can successfully drive the anchor 50 into the annulus or tissue adjacent to the annulus, and (b) the respective anchor launcher 40 is actuated so that the respective anchor launcher 40 drives the anchor 50 into the annulus or tissue adjacent to the annulus. For example, if only the anchors 50 corresponding to the anchor launchers 40 labeled L1 and S4 have not been launched. Steps (a) and (b) in this paragraph are first performed for the L1 anchor, as seen in FIG. 6. Then, steps (a) and (b) are performed for the S4 anchor, as seen in FIG. 7.

The movement of each anchor in step (a) may be implemented by an operator using the manipulating tool 60 based on visual feedback obtained, for example, using echo imaging or fluoro imaging. Alternatively or additionally, the operator may rely on feedback based on signals received from a contact probe (not shown) positioned on whichever anchor launcher 40 is being moved at any given instant. The contact probe provides a real time indication of contact with the tissue (e.g., by sending an electrical signal to the controller 10 shown in FIG. 1).

Figure 8:
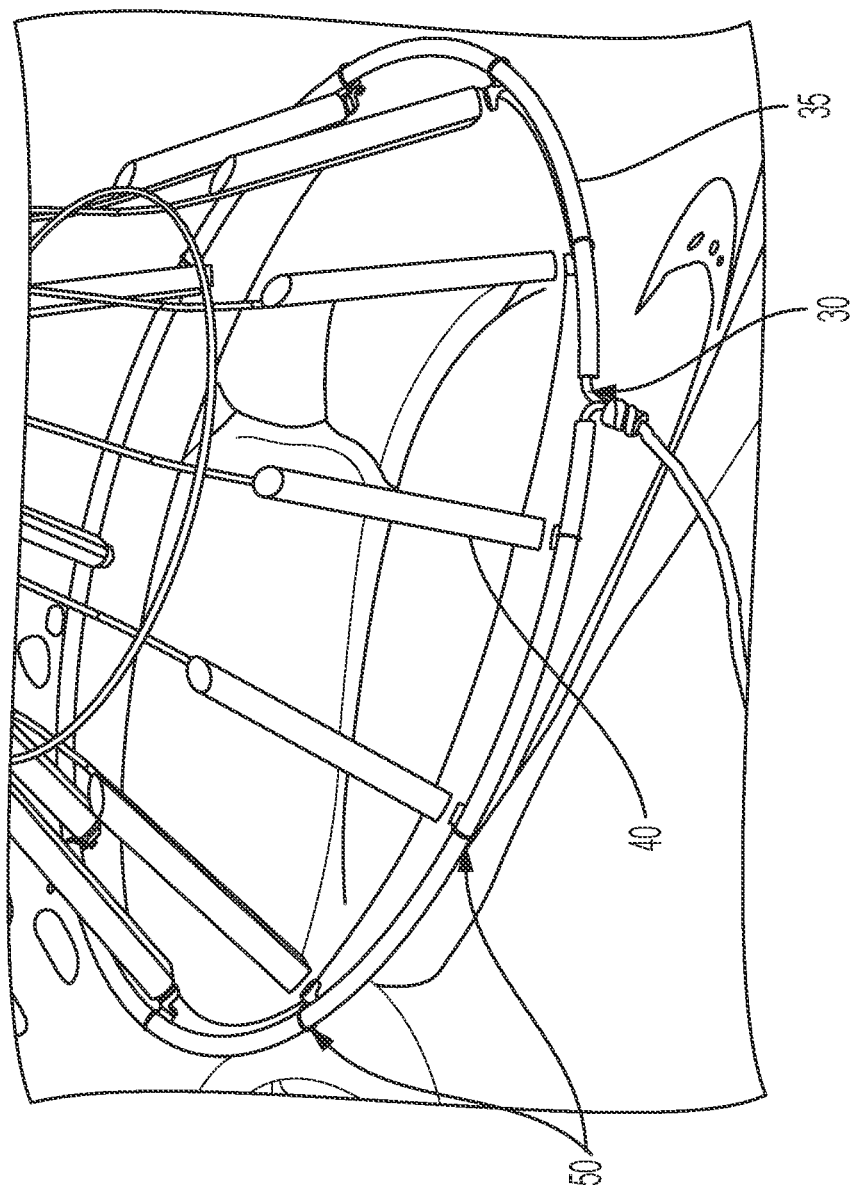
FIG. 8 depicts the FIG. 3 embodiment after the manipulating tool has been withdrawn.
Figure 9:
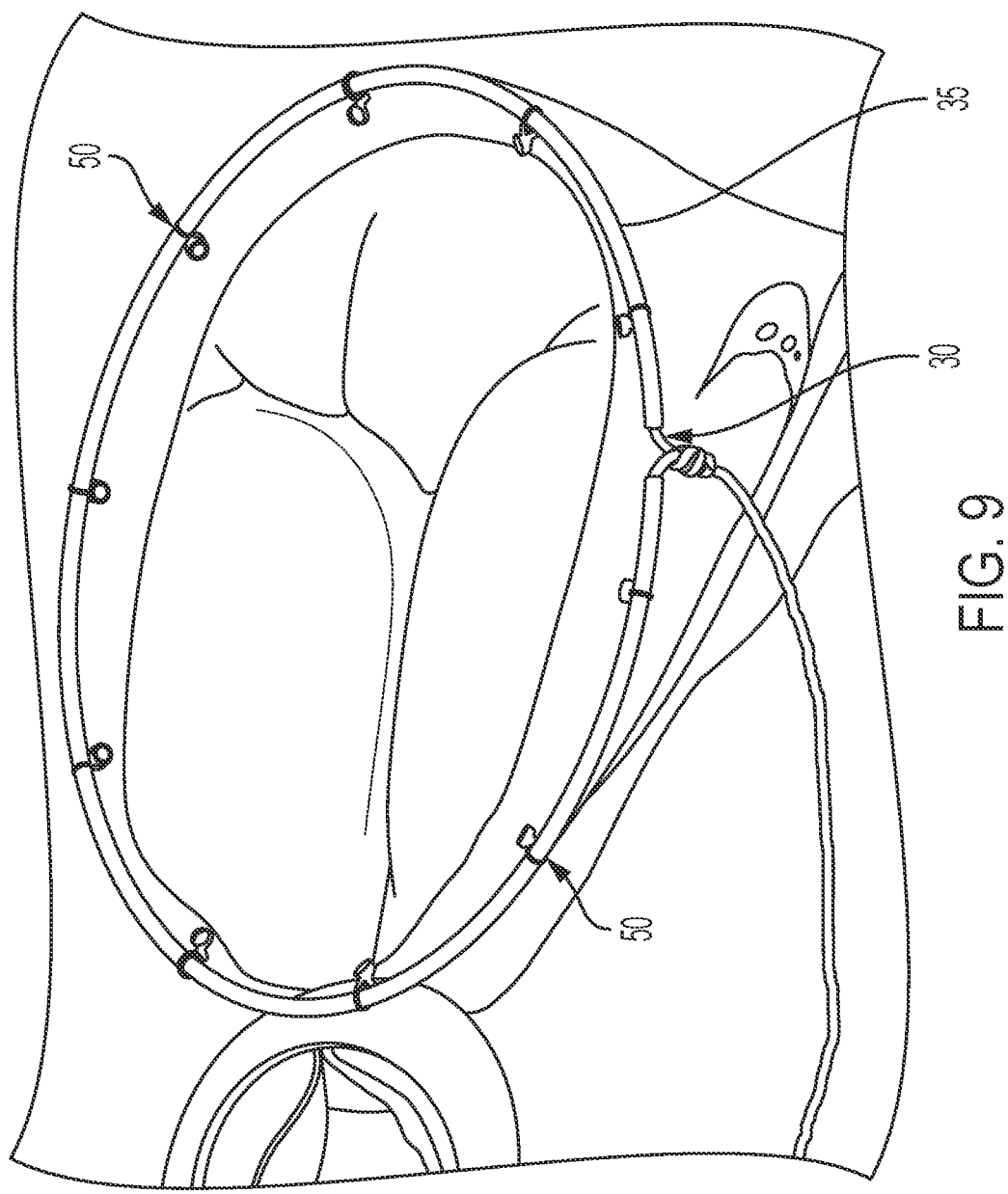
FIG. 9 depicts the FIG. 3 embodiment after the anchor launchers have been withdrawn.

After steps (a) and (b) are performed for all of the anchors that were not launched in the initial batch (i.e., for L1 and S4), the manipulating tool 60 is withdrawn, as seen in FIG. 8. Finally, the anchor launchers 40 are withdrawn, leaving only the flexible cord 30, the optional sleeve 35 surrounding the flexible loop, and the anchors 50 (which have been driven into the annulus or adjacent tissue) behind in the patient's body, as seen in FIG. 9.

Figure 11A:
FIGS. 11A and 11B depict an alternative manipulating tool that may be used instead of the tool shown in FIG. 10.
Figure 11B:
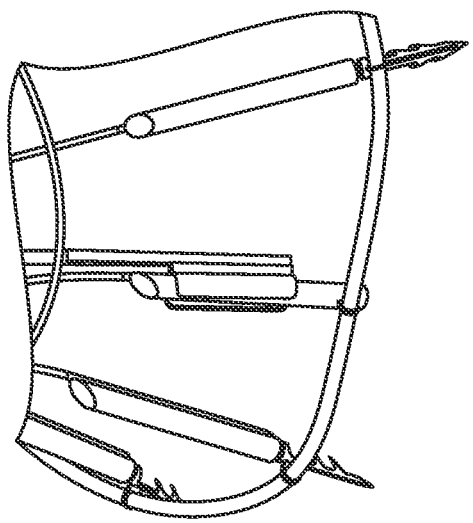
Figure 10:
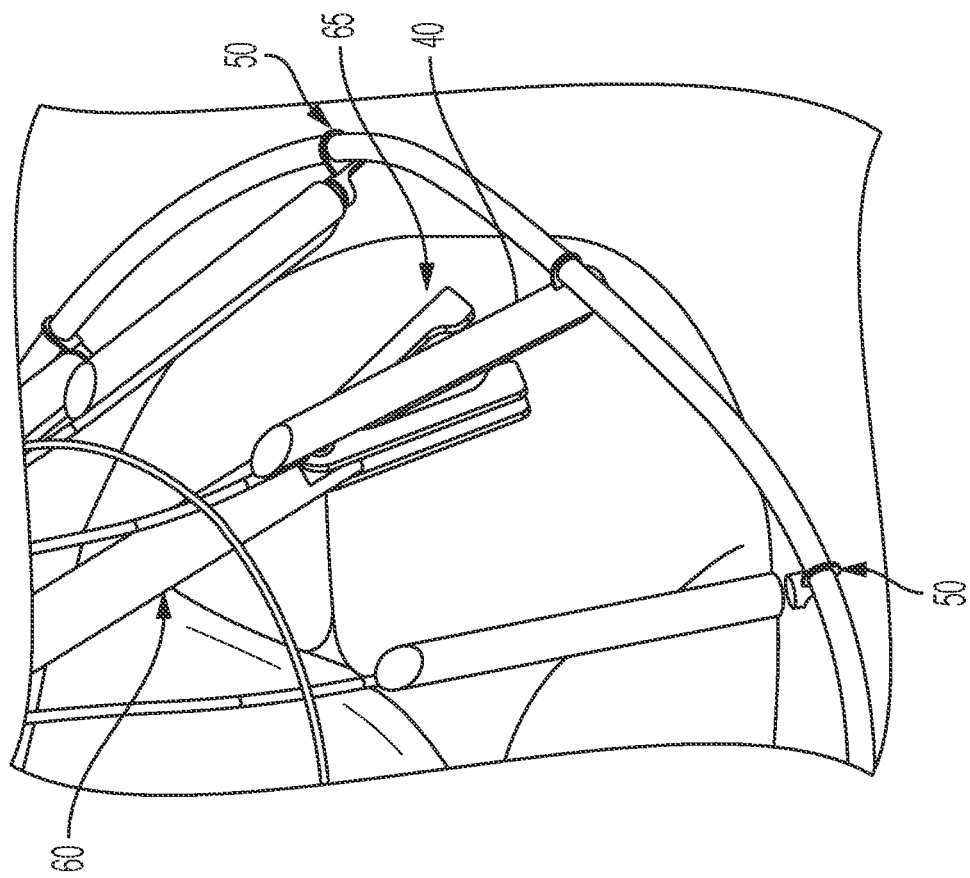
FIG. 10 depicts a detailed view of the manipulating tool depicted in FIGS. 6 and 7.
Figure 13:
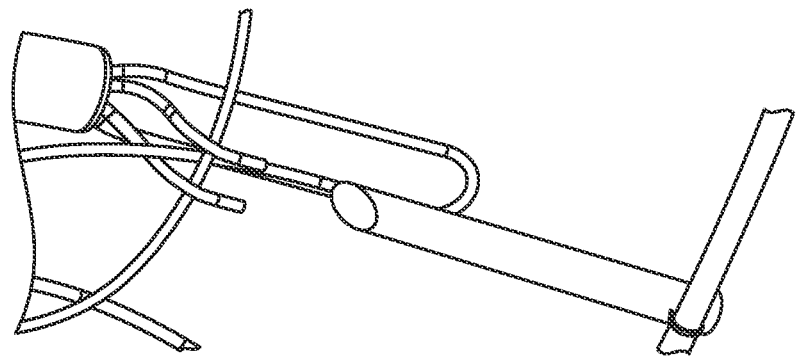
FIG. 13 depicts another alternative manipulating tool that may be used instead of the tool shown in FIG. 10.
Figure 12B:
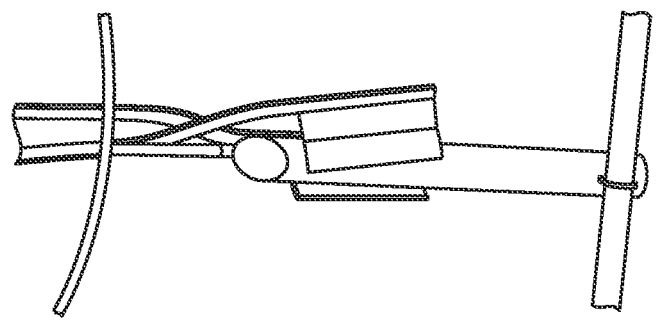
FIGS. 12A and 12B depict another alternative manipulating tool that may be used instead of the tool shown in FIG. 10.
Figure 12A:
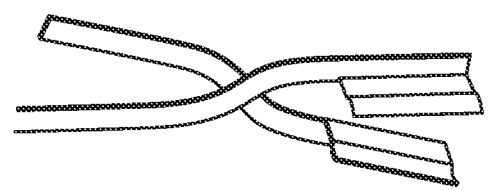

A wide variety of alternatives for implementing the grabber tool 65 can be readily envisioned, including but not limited to the configurations depicted in FIG. 10 (which has jaws that resemble pliers), FIGS. 11A and 11B (which has jaws that resemble a Venus fly trap), FIGS. 12A and 12B (which has jaws that resemble tongs), and FIG. 13 (which has an anchor-launcher holder that resembles a paper clip).

Figure 14:
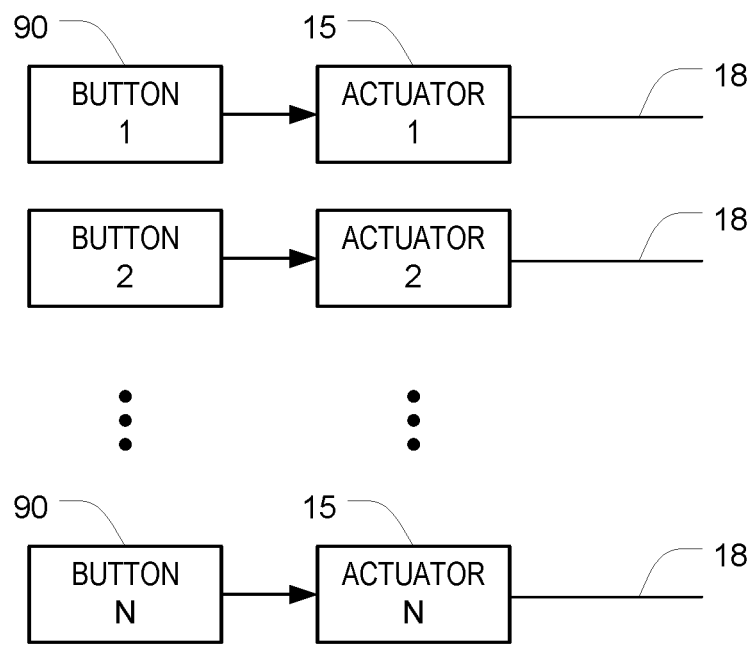
FIG. 14 depicts another example of an approach for implementing individually-controllable actuators.

FIG. 14 is an example of another approach for individually actuating each of the anchor launchers 40. As in the FIG. 1-2 embodiment, an individually controllable actuator 15 is provided for each anchor launcher, and each of those individually controllable actuators 15 pulls on a respective one of the actuation wires 18. And as in the FIG. 1-2 embodiment, the number of actuators 15 will correspond to the number of anchors that are used to affix the cord to the cardiac valve annulus or to adjacent tissue.

In this FIG. 14 embodiment, each of the actuators 15 has its own individual "launch" button 90 (or other user control). And each of these launch buttons 90 is configured, e.g., via a suitable mechanical linkage, so that when the user presses any given launch button 90, the corresponding actuator 15 will pull its respective actuation wire 18. One suitable approach for implementing the actuators 15 is similar to the approach depicted above in connection with FIG. 2A-2B. But instead of using a solenoid with a plunger that, in its extended state, holds the cap 28 in place on the track 22, this FIG. 14 embodiment uses a pin (not shown) that in its initial extended state, holds the cap in place on the track. Pressing each button 90 causes (by operation of the mechanical linkage) the corresponding pin to retract, which has the same effect as retraction of the plunger in the FIG. 2A-2B embodiment.

In this embodiment, it is possible to actuate any desired subset of the N anchor launchers at any given time by pressing the corresponding launch buttons 90. Assume, for example, that there are 8 anchors and the user wants to launch anchors nos. 1-6 but not to launch anchors nos. 7-8. In this case, the user would press only buttons 90 nos. 1-6, which will cause the corresponding actuators 15 nos. 1-6 to pull their respective actuation wires. Those actuation wires 18 will actuate only anchor launchers nos. 1-6, but will not actuate anchor launcher nos. 7-8. At a subsequent time, the unlaunched anchors can be driven into the cardiac valve annulus or adjacent tissue by pressing the corresponding buttons 90 to actuate each of the remaining anchor launchers individually. Because this is similar to the situation described above in connection with the FIGS. 1-2 embodiment (in that independent control over launching is provided for each anchor), the examples described above in connection with FIGS. 3-13 apply with equal force to this FIG. 14 embodiment.

Note that in the embodiments described above in connection with FIGS. 1-14, (i) the position and layout of the flexible cord is adjusted via the catheter until the position and layout of the flexible cord corresponds the annulus, and (ii) the first subset of the N anchor launchers are actuated before the manipulating tool is introduced to the vicinity of the catheter. Thus, at least one of the anchors will be launched without relying on the manipulating tool.

In alternative embodiments, the manipulating tool is relied upon for the launching of ALL of the anchors. In these embodiments, the steps of identifying and actuating that occur prior to the introduction of the manipulating tool in the embodiments described above are omitted. And the step of adjusting a position and layout of the flexible cord via the catheter until the position and layout of the flexible cord corresponds the annulus can optionally also be omitted.

In these embodiments, the flexible cord, the N anchors, and the N anchor launchers are delivered to the vicinity of the annulus via the catheter as in the embodiments described above. The manipulating tool is introduced via the catheter to the vicinity of the annulus. Subsequently, for each of the N anchors in turn, (a) the manipulating tool is used to move the anchor to a position where the respective anchor launcher can successfully drive the anchor into the annulus or tissue adjacent to the annulus, and (b) the respective anchor launcher is actuated so that the respective anchor launcher drives the anchor into the annulus or tissue adjacent to the annulus. As a result of performing steps (a) and (b) for each of the N anchors in turn, all N anchors will be driven into the annulus or tissue adjacent to the annulus, thereby affixing the flexible cord to the annulus.

Optionally, echo imaging or fluoro imaging may be used to determine the position of the anchors while the manipulating tool is being used to move the anchors. Optionally, a set of N contact probes, each of which is affixed to a respective anchor launcher, may be used to determine if each of the respective anchor launchers is making contact with tissue prior to actuating that anchor launcher.

Optionally, subsequent to delivering the flexible cord, the N anchors, and the N anchor launchers, the position and layout of the flexible cord may be adjusted via the catheter until the position and layout of the flexible cord corresponds the annulus. This step may optionally be implemented by inflating a balloon.

In the embodiments described above, the manipulating tool is used to move at least some of the anchor launchers to positions where they can successfully drive the anchor into the annulus or tissue adjacent to the annulus. In contrast, the embodiments described below in connection with FIGS. 15 and 16 move the anchor launchers to their desired position using only catheter steering techniques.

Figure 16:
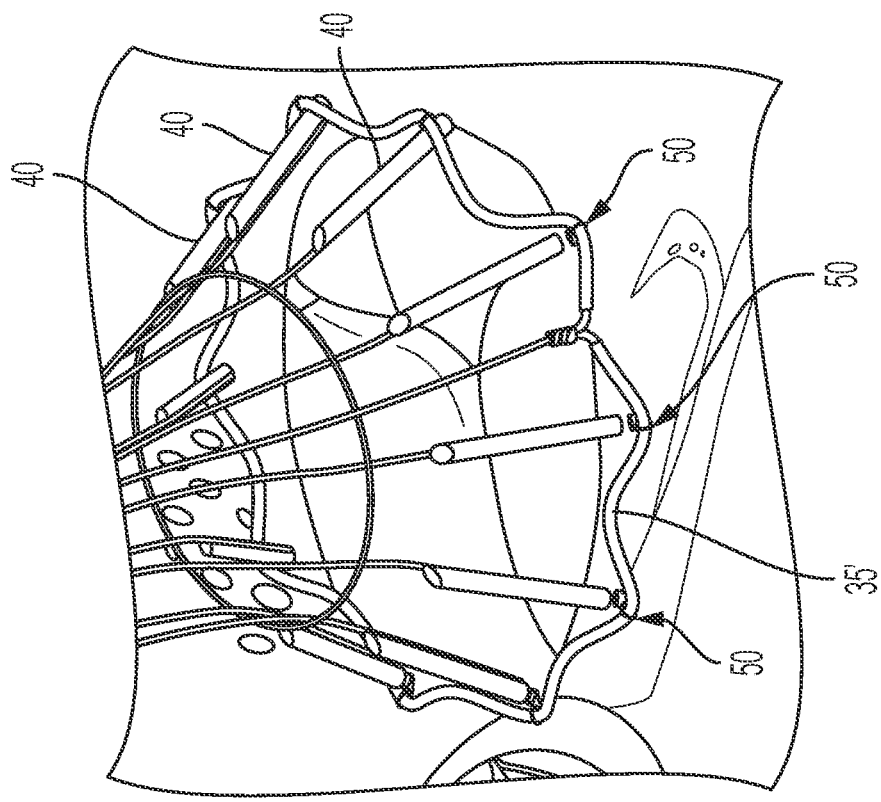
FIG. 16 depicts an overall view of the FIG. 15 embodiment after seven anchors have been launched and three anchors have not been launched.
Figure 15:
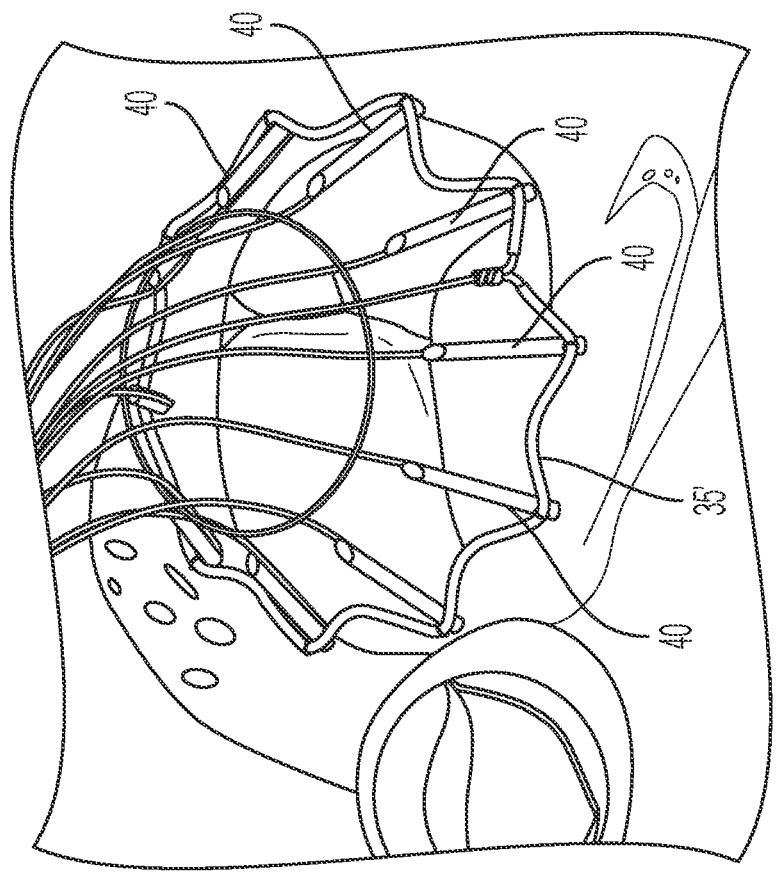
FIG. 15 depicts an example of another annulus-constricting device positioned next to a cardiac valve annulus prior to launching of the anchors, where only seven of the anchor launchers are positioned for launching their respective anchors.

FIGS. 15 and 16 depict an example of affixing an annulus-constricting device to a cardiac valve annulus. In this example, N=10, so there are 10 anchors 50 distributed about the flexible cord 30, and each of those 10 anchors 50 is slidably affixed with respect to the flexible cord 30. In the embodiment depicted in FIGS. 15-16, an optional sleeve 35' made from a material that accepts tissue ingrowth surrounds the flexible cord 30. The flexible cord 30, the optional sleeve 35, the optional balloon (not shown), the anchor launchers 40, and the anchors 50 in these embodiments are the same as the corresponding components in the FIGS. 3-5 embodiments described above, except that the segments of cord 30 and sleeve 35' between any two given anchors 50 have additional slack.

All of these components 30, 35', 40, 50 are delivered to the vicinity of the annulus via a catheter as described above in connection with FIGS. 3-5. Subsequent to the delivering, the position and layout of the flexible cord 30 is adjusted via the catheter (e.g., using catheter steering techniques) until the position and layout of the flexible cord 30 corresponds the annulus, as described above in connection with FIGS. 3-5 and as depicted in FIG. 15.

In the example depicted in FIG. 15, assume that only three anchor launchers 40 are NOT positioned such that the respective anchor launcher can successfully drive the respective anchor into the annulus or tissue adjacent to the annulus, because those three anchor launchers 40 are out of contact with corresponding tissue. The remaining seven anchor launchers 40 ARE positioned such that the respective anchor launcher can successfully drive the respective anchor into the annulus or tissue adjacent to the annulus, because those seven anchor launchers 40 are in contact (or at least close enough) with corresponding tissue.

Subsequent to the position adjusting, a first subset of the anchors 50 (i.e., those anchors which ARE positioned such that the respective anchor launcher can successfully drive the respective anchor into the annulus or tissue adjacent to the annulus) is identified (e.g., as described above in connection with FIGS. 3-5).

Subsequent to the identifying, a first subset of the anchor launchers (i.e., 7 anchor launchers 40 in the present example) that corresponds to the first subset of the anchors 50 is actuated. This causes the first subset of the anchor launchers 40 to drive the first subset of the anchors 50 into the annulus or tissue adjacent to the annulus, resulting in the state depicted in FIG. 16. In the present example, the total number of anchor launchers 40 is 10, and the first subset includes 7 anchors 50. This means that only 3 anchors 50 have not been launched at this point in the procedure.

Subsequent to the actuating of the first subset of the N anchor launchers, for each of the N anchors that have not yet been driven into the annulus or tissue adjacent to the annulus, catheter steering techniques are used to adjust a position of a respective corresponding anchor launcher to a position where the respective corresponding anchor launcher can successfully drive the anchor into the annulus or tissue adjacent to the annulus; and the respective corresponding anchor launcher is actuated so that the respective corresponding anchor launcher drives the anchor into the annulus or tissue adjacent to the annulus. The steps described in the following paragraphs is an example of this approach.

Subsequent to the actuating of the first subset of the N anchor launchers, the scaffold of arms that support the anchor launchers may collapse (fully or partially) because most of the anchors 50 that are attached to the flexible cord 30 are no longer held in place by their respective anchor launchers 40. Alternatively, in some embodiments, the scaffold of arms may be made from a soft metal that retains its shape after the majority of the anchors 50 have been launched. But the position of the anchor launchers 40 and the scaffold of arms that support the anchor launchers can still be adjusted using conventional catheter steering techniques. These conventional catheter steering techniques are used by the practitioner to manipulate the remaining anchor launchers 40 to corresponding desired positions (i.e., to positions where the corresponding anchors 50 can be driven into the annulus or adjacent tissue).

More specifically, subsequent to the actuating of the first subset of anchor launchers, (a) catheter steering techniques are used to move the entire assembly to a new position at which one or more of the unlaunched anchors is in a position where the respective anchor launcher 40 can successfully drive the unlaunched anchor(s) 50 into the annulus or tissue adjacent to the annulus, and (b) the respective corresponding anchor launcher(s) 40 is/are actuated so that the respective anchor launcher(s) 40 drives one or more of the unlaunched anchors 50 into the annulus or tissue adjacent to the annulus. For example, if three anchors 50 have not been previously launched, steps (a) and (b) in this paragraph might (i) bring only two of those three anchors into the suitable position and (ii) drive those two anchors into the annulus or tissue adjacent to the annulus. In this situation, steps (a) and (b) are repeated one additional time to bring the last anchor into the suitable position and drive the last anchor into the annulus or tissue adjacent to the annulus. If, on the other hand, the first occurrence of steps (a) and (b) in this paragraph successfully brought all three unlaunched anchors into the suitable position and drove all three of those anchors into the annulus or tissue adjacent to the annulus, there would be no need to repeat steps (a) and (b). Alternatively, if the first occurrence of steps (a) and (b) in this paragraph successfully brought only one of the unlaunched anchors into the suitable position and drove that one anchor into the annulus or tissue adjacent to the annulus, it might be necessary to repeat steps (a) and (b) two additional times.

The operator's control of the position of any given anchor in step (a) may rely on visual feedback obtained, for example, using echo imaging or fluoro imaging. Alternatively or additionally, the operator may rely on feedback based on signals received from a contact probe as described above in connection with the FIG. 3-5 embodiment.

Steps (a) and (b) are performed as many times as necessary until all of the anchors have been brought into a suitable position and driven into the annulus or tissue adjacent to the annulus. Finally, the anchor launchers 40 are withdrawn, leaving only the flexible cord 30, the optional sleeve 35 surrounding the flexible loop, and the anchors 50 (which have been driven into the annulus or adjacent tissue) behind in the patient's body, similar to the situation described above in connection with FIG. 9.

Notably, the extra slack in the flexible cord 30 and the optional sleeve 35 depicted in FIGS. 15 and 16 is helpful to prevent dislodgment of any anchors that have already been driven into the annulus or tissue adjacent to the annulus when catheter steering techniques are used to adjust the position of any anchor launchers that still contain unlaunched anchors. Optionally, similar slack may be added to the FIG. 3-5 embodiment described above.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of affixing a device to a cardiac valve annulus, the method comprising:
    delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus;
    subsequent to the delivering, adjusting a position and layout of the flexible cord via the catheter until the position and layout of the flexible cord corresponds the annulus;
    subsequent to the adjusting, identifying a first subset of the N anchors which are positioned such that the respective anchor launcher can successfully drive the respective anchor into the annulus or tissue adjacent to the annulus, wherein the first subset includes fewer than N anchors;
    subsequent to the identifying, actuating a first subset of the N anchor launchers that corresponds to the first subset of the N anchors, so that the first subset of the N anchor launchers drive the first subset of the N anchors into the annulus or tissue adjacent to the annulus;

introducing a manipulating tool via the catheter to the vicinity of the annulus; and subsequent to the actuating of the first subset of the N anchor launchers, for each of the N anchors that have not yet been driven into the annulus or tissue adjacent to the annulus, (a) using the manipulating tool to move the anchor to a position where the respective anchor launcher can successfully drive the anchor into the annulus or tissue adjacent to the annulus, and (b) actuating the respective anchor launcher so that the respective anchor launcher drives the anchor into the annulus or tissue adjacent to the annulus.

2. The method of claim 1, wherein each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

3. The method of claim 1, wherein the identifying step comprises at least one of echo imaging and fluoro imaging.

4. The method of claim 1, wherein the identifying step comprises determining whether a contact probe that is affixed to each of the anchor launchers is making contact with tissue.

5. The method of claim 1, wherein the actuating of the first subset of the N anchor launchers comprises actuating the entire first subset of the N anchor launchers substantially simultaneously.

6. The method of claim 1, wherein the step of adjusting the position and layout of the flexible cord comprises inflating a balloon.

7. The method of claim 1, wherein the first subset includes at least two anchors.

8. A method of affixing a device to a cardiac valve annulus, the method comprising:

delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus;

subsequent to the delivering, adjusting a position and layout of the flexible cord via the catheter until the position and layout of the flexible cord corresponds the annulus;

subsequent to the adjusting, identifying a first subset of the N anchors which are positioned such that the respective anchor launcher can successfully drive the respective anchor into the annulus or tissue adjacent to the annulus, wherein the first subset includes fewer than N anchors;

subsequent to the identifying, actuating a first subset of the N anchor launchers that corresponds to the first subset of the N anchors, so that the first subset of the N anchor launchers drive the first subset of the N anchors into the annulus or tissue adjacent to the annulus; and subsequent to the actuating of the first subset of the N anchor launchers, for each of the N anchors that have not yet been driven into the annulus or tissue adjacent to the annulus, (a) using catheter steering techniques to adjust a position of a respective corresponding anchor launcher to a position where the respective corresponding anchor launcher can successfully drive the anchor into the annulus or tissue adjacent to the annulus, and (b) actuating the respective corresponding anchor launcher so that the respective corresponding anchor launcher drives the anchor into the annulus or tissue adjacent to the annulus.

9. The method of claim 8, wherein steps (a) and (b) are performed at least twice, and wherein steps (a) and (b) are repeated until all of the anchors have been driven into the annulus or tissue adjacent to the annulus.

10. The method of claim 8, wherein each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

11. The method of claim 8, wherein the identifying step comprises at least one of echo imaging and fluoro imaging.

12. The method of claim 8, wherein the identifying step comprises determining whether a contact probe that is affixed to each of the anchor launchers is making contact with tissue.

13. The method of claim 8, wherein the actuating of the first subset of the N anchor launchers comprises actuating the entire first subset of the N anchor launchers substantially simultaneously.

14. The method of claim 8, wherein the first subset includes at least two anchors.

15. A method of affixing a device to a cardiac valve annulus, the method comprising:

delivering a flexible cord, N anchors, and N anchor launchers to the vicinity of the annulus via a catheter, wherein N is an integer greater than 4, wherein the N anchors are distributed about the flexible cord, wherein each of the N anchors is affixed with respect to the flexible cord, and wherein each of the N anchor launchers is configured to, upon actuation, drive a respective one of the N anchors into the annulus or tissue adjacent to the annulus;

introducing a manipulating tool via the catheter to the vicinity of the annulus; and for each of the N anchors in turn, (a) using the manipulating tool to move the anchor to a position where the respective anchor launcher can successfully drive the anchor into the annulus or tissue adjacent to the annulus, and (b) actuating the respective anchor launcher so that the respective anchor launcher drives the anchor into the annulus or tissue adjacent to the annulus.

16. The method of claim 15, wherein each of the N anchors is slidably affixed with respect to the flexible cord and is configured so that when a respective anchor is driven into the annulus or tissue adjacent to the annulus by a respective anchor launcher, the respective anchor will slide from an initial position to a final position at which the respective anchor fastens a respective portion of the flexible cord to the annulus or to the tissue adjacent to the annulus.

17. The method of claim 15, further comprising using at least one of echo imaging and fluoro imaging to determine the position of the anchors while the manipulating tool is being used to move the anchors.

18. The method of claim 15, further comprising determining whether a contact probe that is affixed to each of the anchor launchers is making contact with tissue.

19. The method of claim 15, further comprising:
subsequent to the delivering, adjusting a position and layout of the flexible cord via the catheter until the position and layout of the flexible cord corresponds the annulus.

20. The method of claim 15, wherein the step of adjusting a position and layout of the flexible cord comprises inflating a balloon.

* * * * *